(12) United States Patent
Polack

(10) Patent No.: US 12,390,029 B2
(45) Date of Patent: Aug. 19, 2025

(54) BLACKOUT PILLOWCASE COVER APPARATUS

(71) Applicant: John Polack, Brooklyn, NY (US)

(72) Inventor: John Polack, Brooklyn, NY (US)

( * ) Notice: Subject to any disclaimer, the term of this patent is extended or adjusted under 35 U.S.C. 154(b) by 284 days.

(21) Appl. No.: 18/310,565

(22) Filed: May 2, 2023

(65) Prior Publication Data

US 2024/0188737 A1    Jun. 13, 2024

Related U.S. Application Data

(60) Provisional application No. 63/431,674, filed on Dec. 10, 2022.

(51) Int. Cl.
*A47G 9/02* (2006.01)
*A61F 9/04* (2006.01)

(52) U.S. Cl.
CPC ........... *A47G 9/0253* (2013.01); *A61F 9/04* (2013.01)

(58) Field of Classification Search
CPC .............................. A47G 9/0253; A61G 9/04
See application file for complete search history.

(56) References Cited

U.S. PATENT DOCUMENTS

| | | | | |
|---|---|---|---|---|
| 1,380,480 A * | 6/1921 | Jennings | A47C 7/383 | 5/490 |
| 2,412,769 A * | 12/1946 | Easterbrooks | A47G 9/0253 | 5/636 |
| D270,320 S * | 8/1983 | Smith | A47G 9/0253 | D6/601 |
| 4,420,847 A * | 12/1983 | Smith | A47G 9/0253 | 5/490 |
| 5,127,117 A * | 7/1992 | Bridges | A47G 9/10 | 5/636 |
| 5,572,753 A * | 11/1996 | Ruscitto | A47G 9/0253 | 112/475.08 |
| 6,363,554 B1 * | 4/2002 | Brown | A47G 9/0253 | 5/636 |
| 2008/0216244 A1 * | 9/2008 | Minton | A47G 9/10 | 5/636 |
| 2013/0312180 A1 * | 11/2013 | Moran | A47G 9/0253 | 5/490 |
| 2014/0326188 A1 * | 11/2014 | Isaac | A01K 1/0353 | 119/28.5 |
| 2016/0302595 A1 * | 10/2016 | Francois | A47G 9/0253 | |
| 2017/0105555 A1 * | 4/2017 | Lukin, Jr. | A47G 9/0253 | |

FOREIGN PATENT DOCUMENTS

| | | | | |
|---|---|---|---|---|
| WO | WO-2020016883 A1 * | 1/2020 | | A61F 9/045 |
| WO | WO-2022116231 A1 * | 6/2022 | | |

* cited by examiner

*Primary Examiner* — Eric J Kurilla

(57) ABSTRACT

A blackout cover for use with a pillow and/or pillowcase is disclosed. The cover includes a breathable or non-breathable pillowcase with an integrated blackout cover means that can be deployed over a person's face and eyes to block light and improve sleep. The blackout cover means includes an opening for the nose and optional ear slots to prevent the cover from sliding down the face and blocking the nostrils. The cover can be attached to a pillowcase or pillow by various means, such as stitches, snaps, or ribbon attachments, and can be adjusted using straps and slider adjustment means. The cover can also have multiple blackout layers for improved light blocking capabilities. Additionally, the cover can be used in combination with an eye mask case holder means or a strap attachment means to offer alternate light-blocking embodiments.

7 Claims, 8 Drawing Sheets

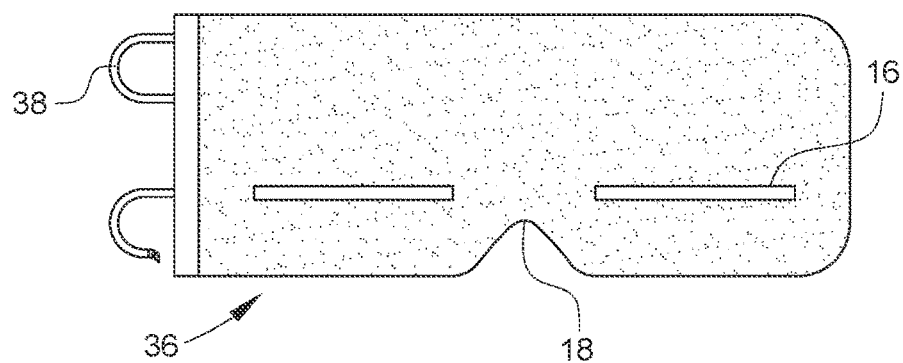
FIG. 7
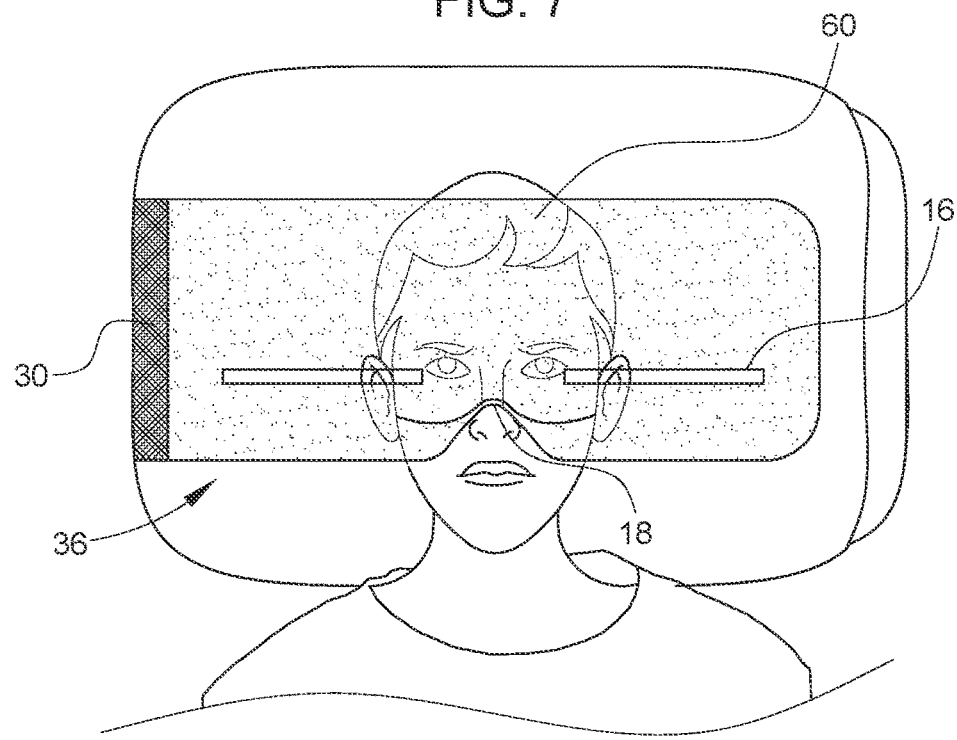
FIG. 8
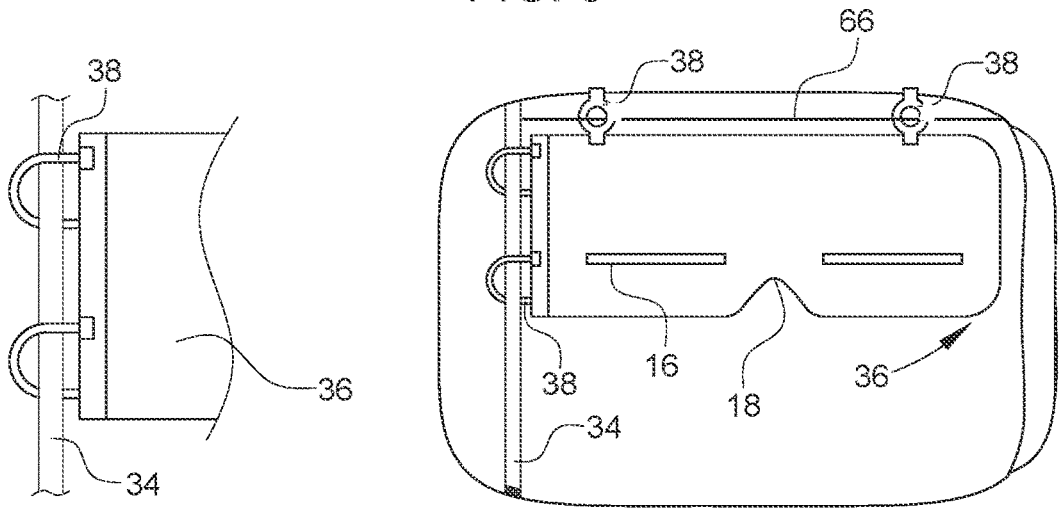
FIG. 9
FIG. 10

BLACKOUT PILLOWCASE COVER APPARATUS

CROSS REFERENCE TO RELATED APPLICATIONS

This patent application claims the benefit of U.S. provisional Application No. 63/431,674, filed Dec. 10, 2022.

FIELD OF INVENTION

The present invention relates generally to a blackout cover apparatus. More specifically, the present invention relates to a blackout apparatus configured to be integrated with or attached to a pillowcase.

BACKGROUND

Sleep deprivation is a widespread problem affecting millions of people worldwide. When the sun rises, its light can penetrate through windows and blinds, causing sleep disruption for those who want to continue sleeping. The lack of sleep can lead to poor productivity during the day and long-term health issues. While some people buy eye masks to block sunlight, these can be easily misplaced and can fall off when a person rolls over during sleep. Additionally, some people find them uncomfortable to wear for extended periods.

Blackout curtains are another solution to block light, but they can be difficult to install, especially in rented living spaces where alterations are prohibited. They can also be expensive and bulky, making them impractical for those who frequently move or travel.

In light of the above, there is a need for a practical and effective solution to block light and promote restful sleep.

USD958233S discloses a standard blackout sleep mask with a cavity formed to encompass the eyes and a strap to hold the mask against a wearer's face.

US2019231595A1 describes a sleep mask with features including tension reduction from the securing bands, a light blocking pillow, ergonomic/pre-curved shaping, an eye space, ear comfort features, slip over comfort which can account for various hair styles and various head positions of the wearer, and therapeutic, beauty and relaxing features.

U.S. Pat. No. 8,239,987B2 describes a neck cushion device with associated eye mask and headrest cushion for improved comfort while sleeping in an upright position. The device comprises a standard neck pillow having a general C-shape and internal cushioning, attached to an upstanding headrest and deployable eye mask. The headrest secures to the neck pillow via a closed loop, wherein the neck pillow is inserted therethrough. The neck pillow is secured around the neck of a user, while the headrest is positioned between the back of a user's head and a seat to provide upright support. The eye mask is deployable from a pouch along the back of the headrest, and is attached via a band of fabric to prevent its misplacement. The user is provided comfort by properly supporting their head along the neck and behind the head, while the eye mask provides a blind for darkened sleeping.

None of the prior art discloses apparatus with light blocking functionality which is also configured for integration with a pillow or pillowcase. The invention of a blackout cover, such as a pillowcase with a built-in cover, could provide a simple and easy-to-use solution.

It is within this context that the present invention is provided.

SUMMARY

The present disclosure provides a blackout cover for use with a pillow and/or pillowcase. The cover includes a breathable or non-breathable pillowcase with an integrated blackout cover means that can be deployed over a person's face and eyes to block light and improve sleep. The blackout cover means includes an opening for the nose and optional ear slots to prevent the cover from sliding down the face and blocking the nostrils especially when the user turns sideways. The cover can be attached to a standard pillowcase or pillow by various means, such as stitches, snaps, clips, fabric or ribbon attachments made of fabric or elastic, and can be adjusted using straps and slider adjustment means. The cover can also have multiple blackout layers for improved light blocking capabilities. Additionally, the cover can be used in combination with an eye mask means with a strap attachment means to offer alternate light-blocking embodiments.

According to a first aspect of the present disclosure, there is provided a blackout cover apparatus for a pillowcase, the apparatus comprising: a blackout cover means; and an attachment mechanism specifically configured for coupling the blackout cover means to the surface of a pillowcase.

In some embodiments, the attachment means for coupling the blackout cover means to a pillowcase is of a detachable type.

For example, the attachment means may comprise one or more loops. The one or more loops may be elastic, and may be of adjustable length. The one or more loops may also be arranged in coordination with a set of adjustment straps so as to enable the user to pull the straps to adjust the length of the blackout cover means and control how much of the pillowcase is covered. The one or more loops may also be fabric into which a pillow or pillowcase can be inserted.

Alternatively or additionally the attachment means may comprise one or more hooks such as strap that loops around the pillowcase at the side for coupling the hooks to, and/or Velcro® straps or adhesive.

In some embodiments, further comprising the pillowcase itself, the attachment means for coupling to the pillowcase may be of a permanent connection type.

In such examples the attachment means may comprise stitches. They may also include a ribbon stitched at either end connecting the blackout means to the pillowcase.

In some embodiments, the blackout cover means comprises a fabric cover. The fabric cover may comprise one or more openings for the ears, mouth, or nose. The fabric cover may also be formed of a breathable material. The perimeter of the fabric cover may be elasticized.

In other embodiments, the blackout cover means is a blackout eye mask.

In yet further embodiment, the blackout cover means is an eyemask holder containing a removable eye mask.

In some embodiment, the blackout cover apparatus further comprises one or more snap button fittings for securing portions of the blackout cover means to the pillowcase.

In some embodiment, the blackout cover means is dark and is composed of one of silk, cotton, nylon, mixed or related fabric or material.

BRIEF DESCRIPTION OF THE DRAWINGS

Various embodiments of the invention are disclosed in the following detailed description and accompanying drawings.

FIG. 7 illustrates a top perspective view of the right side of the side-connecting blackout cover in a second embodiment, with an opening for the nose, ear slots, and a strap attachment means.

FIG. 8 illustrates another top perspective view of the right side of the side-connecting black out cover of the second embodiment, illustrating an opening for the nose, ear slots, stitches used for attachment, and the blackout cover covering a person's face.

FIG. 9 illustrates a right-side view of the side-connecting blackout cover of the second embodiment, displaying a slide-on pillowcase strap overlay means hook, and a strap attachment means.

FIG. 10 illustrates a top perspective view of the right side of the slide on side-connecting blackout cover of the second embodiment, showing an opening for the nose, ear slots, pillowcase strap overlay means hook, top pillowcase slide-on strap overlay means hook, and strap attachment means.

Figure 1:
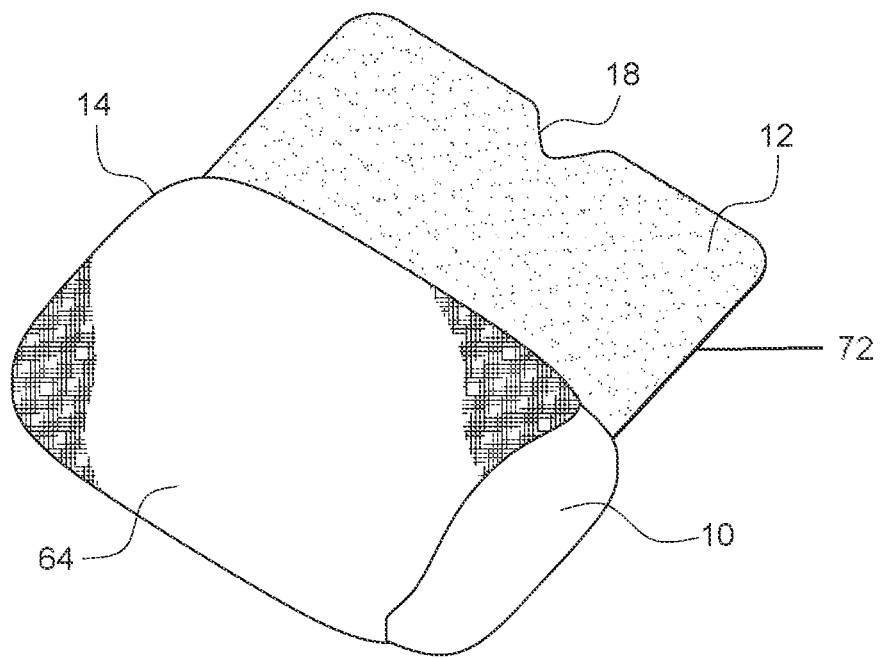
FIG. 1 illustrates the preferred embodiment of the invention in a top perspective view. It includes a blackout pillowcase with a folded open blackout cover, an opening for the nose, a pillow, and the pillowcase itself.

Common reference numerals are used throughout the figures and the detailed description to indicate like elements. One skilled in the art will readily recognize that the above figures are examples and that other architectures, modes of operation, orders of operation, and elements/functions can be provided and implemented without departing from the characteristics and features of the invention, as set forth in the claims.

DETAILED DESCRIPTION AND PREFERRED EMBODIMENT

The following is a detailed description of exemplary embodiments to illustrate the principles of the invention. The embodiments are provided to illustrate aspects of the invention, but the invention is not limited to any embodiment. The scope of the invention encompasses numerous alternatives, modifications and equivalent; it is limited only by the claims.

Numerous specific details are set forth in the following description in order to provide a thorough understanding of the invention. However, the invention may be practiced according to the claims without some or all of these specific details. For the purpose of clarity, technical material that is known in the technical fields related to the invention has not been described in detail so that the invention is not unnecessarily obscured.

Definitions

The terminology used herein is for the purpose of describing particular embodiments only and is not intended to be limiting of the invention.

As used herein, the term "and/or" includes any combinations of one or more of the associated listed items.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

The terminology used herein is for the purpose of describing particular embodiments only and is not intended to be limiting. As used herein, the singular forms "a," "an" and "the" are intended to include the plural forms as well, unless the context clearly indicates otherwise.

The terms "first," "second," and the like are used herein to describe various features or elements, but these features or elements should not be limited by these terms. These terms are only used to distinguish one feature or element from another feature or element. Thus, a first feature or element discussed below could be termed a second feature or element, and similarly, a second feature or element discussed below could be termed a first feature or element without departing from the teachings of the present disclosure.

FIG. 1 displays a top perspective view of the preferred embodiment of the blackout cover. The blackout pillowcase 14 is shown with its blackout cover means 12 in a folded open state, revealing the underside of the cover. The blackout cover means 12 is made of at least one or more layers 72 of blackout material, which can be breathable cotton, silk, nylon, or similar materials, and may also be made of non-breathable fabrics. The blackout cover means 12 can either be attached or integral to a standard pillowcase 64. It is designed to cover a person's head, face, including the eyes, and can be easily folded over the head and eyes to, as best as possible, block out light that disturbs sleep. The nose opening 18 cut out of the blackout cover means 12 helps prevent the cover from obstructing the entrance to a person's nose and aids in the cover's stability on the face when a person turn sideways. In this view, a pillow 10 is shown with the majority of it inside a pillowcase 64.

Figure 2:
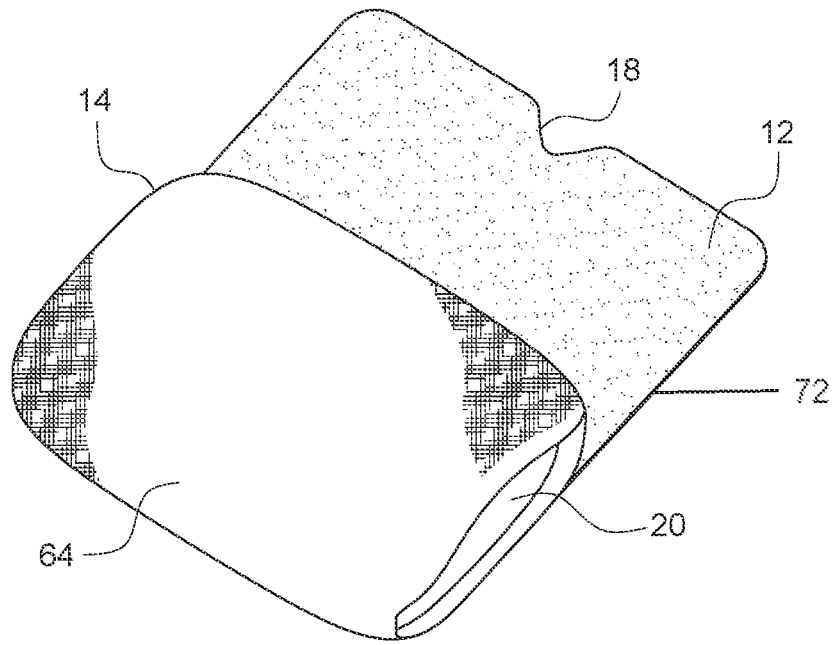
FIG. 2 illustrates a similar perspective of the same embodiment, showing the blackout cover, the pillowcase, an opening for the nose, and an opening for the pillow.
Figure 15:
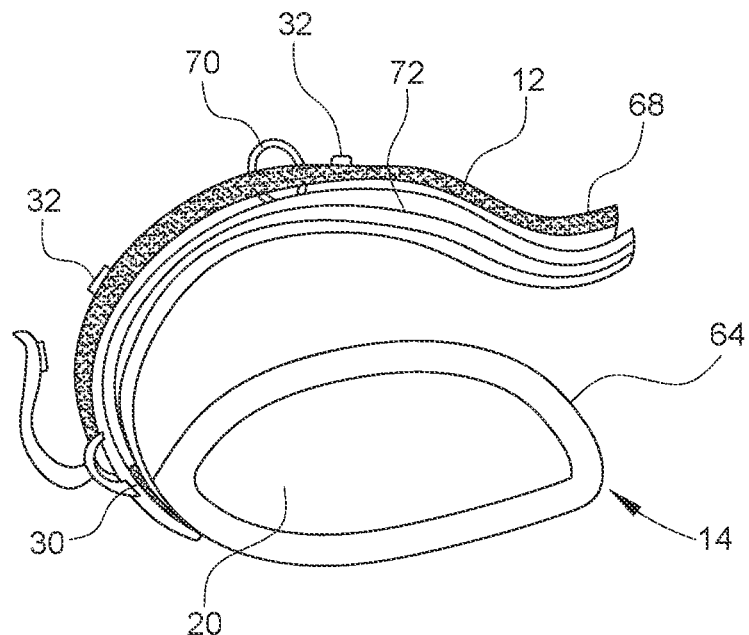
FIG. 15 illustrates a blackout pillowcase and a single layer pillowcase from a left side view, with a pillowcase opening, a multiple layer blackout cover means, nose opening, stitches means of attachment, an adjustment strap, strap loops, snap button means for attachment, and a blackout material means layer example. The multiple layers of blackout material provide maximum darkness for sleeping.

In FIG. 2, we can see a top perspective view of the blackout pillowcase 14 with its blackout cover means 12 in a folded open state, showing the underside of the blackout cover means 12. The blackout pillowcase 14 is a pillowcase 64 that has a blackout cover means 12 made of at least one or more layers 72 (as shown in FIG. 15) of dark breathable cotton, silk, nylon or similar materials, but can also be made of non-breathable fabrics. The blackout cover means 12 can either be attached to a standard pillowcase 64 or be integral to it. The blackout cover means 12 can be used to cover all or a portion of a person's head and face including the eyes to block as much light as possible. This view also shows an optional opening in the blackout cover means 12, called the opening for nose 18, which rests over the bridge of a person's nose. This opening helps with cover stability and prevents the blackout cover means 12 from covering the entrance to a person's nose.

Figure 3:
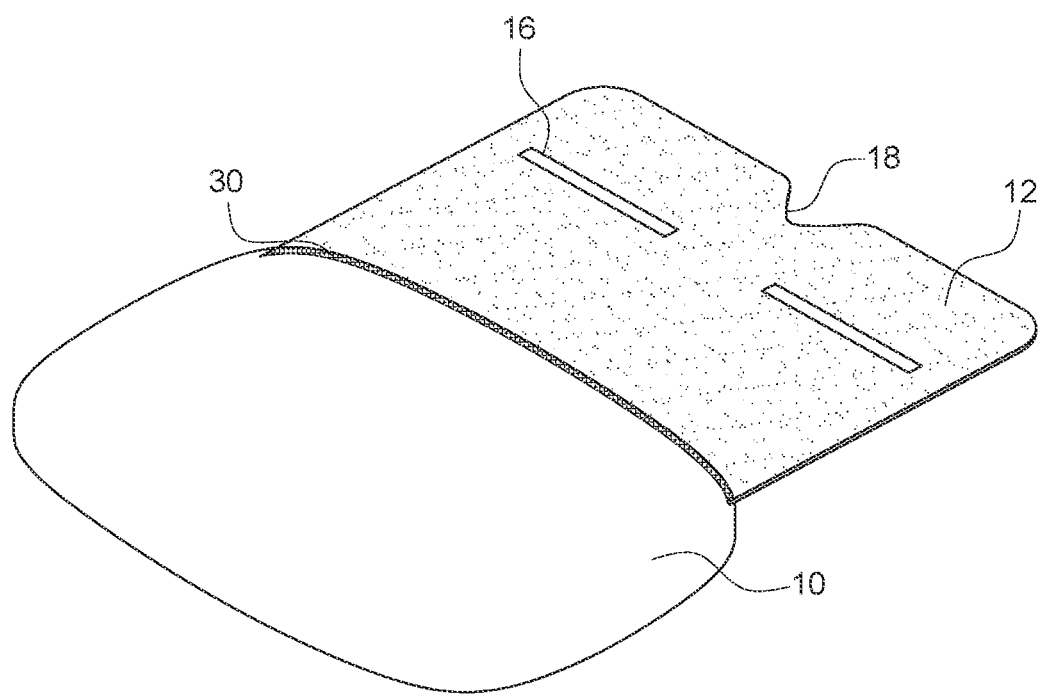
FIG. 3 illustrates a top perspective view of a blackout pillow without a pillowcase, presenting the folded open blackout cover, stitches used for attachment, an opening for the nose, and dual ear slots.

FIG. 3, a top perspective view of a pillow 10, lacking a pillowcase, is presented. The pillow 10 is attached to a blackout cover means 12 by a means of attachment 30, such as stitches. The blackout cover means 12, made of breathable cotton, silk, nylon or similar materials, can also be made of non-breathable fabric means. The purpose of the blackout cover means 12 is to obstruct the effects of light which can disturb or hinder sleep by covering all or a part of a person's face, including their eyes. An opening in the blackout cover means 12, referred to as the opening for nose 18, rests over the bridge of a person's nose, aiding in cover stability and helping to prevent the cover from obstructing the entrance to their nostrils. Additionally, at least one optional ear slot means 16 is visible in the view, which is a cutout in the blackout cover means 12 used as a stabilization method by slipping over the ear. The ear slot means 16 works independently or in combination with the opening for nose 18 to prevent the pillowcase cover from slipping too far down a person's face and obstructing the entrance to their nostrils. To cover the head and eyes, the blackout cover means 12 can be grabbed or folded over the face.

Figure 4:
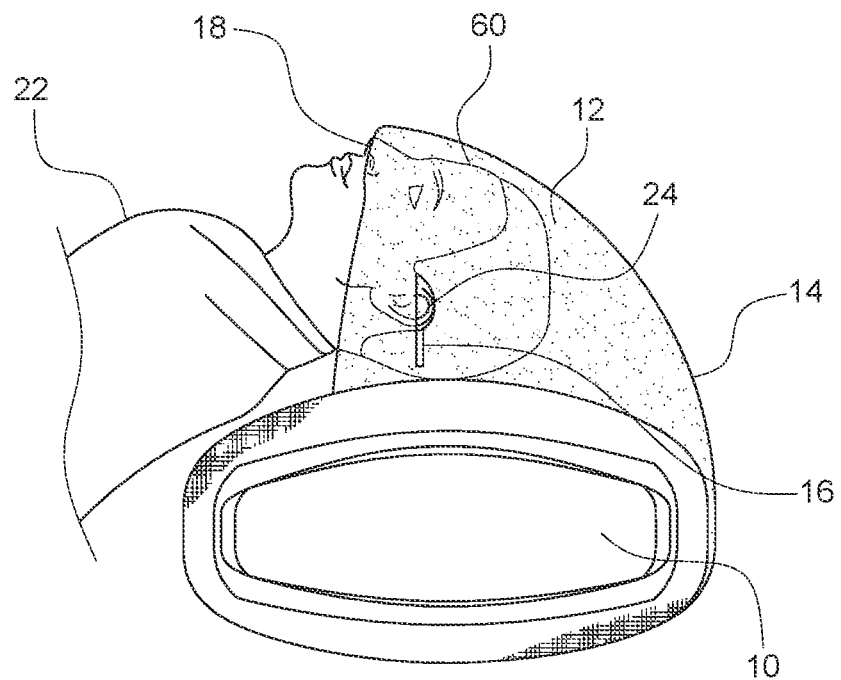
FIG. 4 illustrates a left-side view of a person resting on a blackout pillowcase with a pillow inside. The figure shows the blackout cover covering the head, an opening for the nose, and an ear protruding from the ear slot. In this illustration the blackout cover is one with the fabric.

FIG. 4 depicts a lateral view of an individual's head 60 resting on a blackout pillowcase 14, with an integrated and deployed blackout cover means 12 covering a section of the head. The view illustrates an opening for nose 18 created by cutting out a portion of the blackout cover means 12, allowing for unrestricted breathing while the cover is in use. Moreover, an optional ear slot means 16 is visible, which helps to further prevent the blackout cover means 12 from slipping down a person's face. In this view, an ear 24 protruding from the ear slot means 16 is apparent. This figure also displays a pillow 10 covered by the blackout pillowcase 14. Also seen is this view is the blackout cover means 12 in an integrated state with the fabric.

Figure 5:
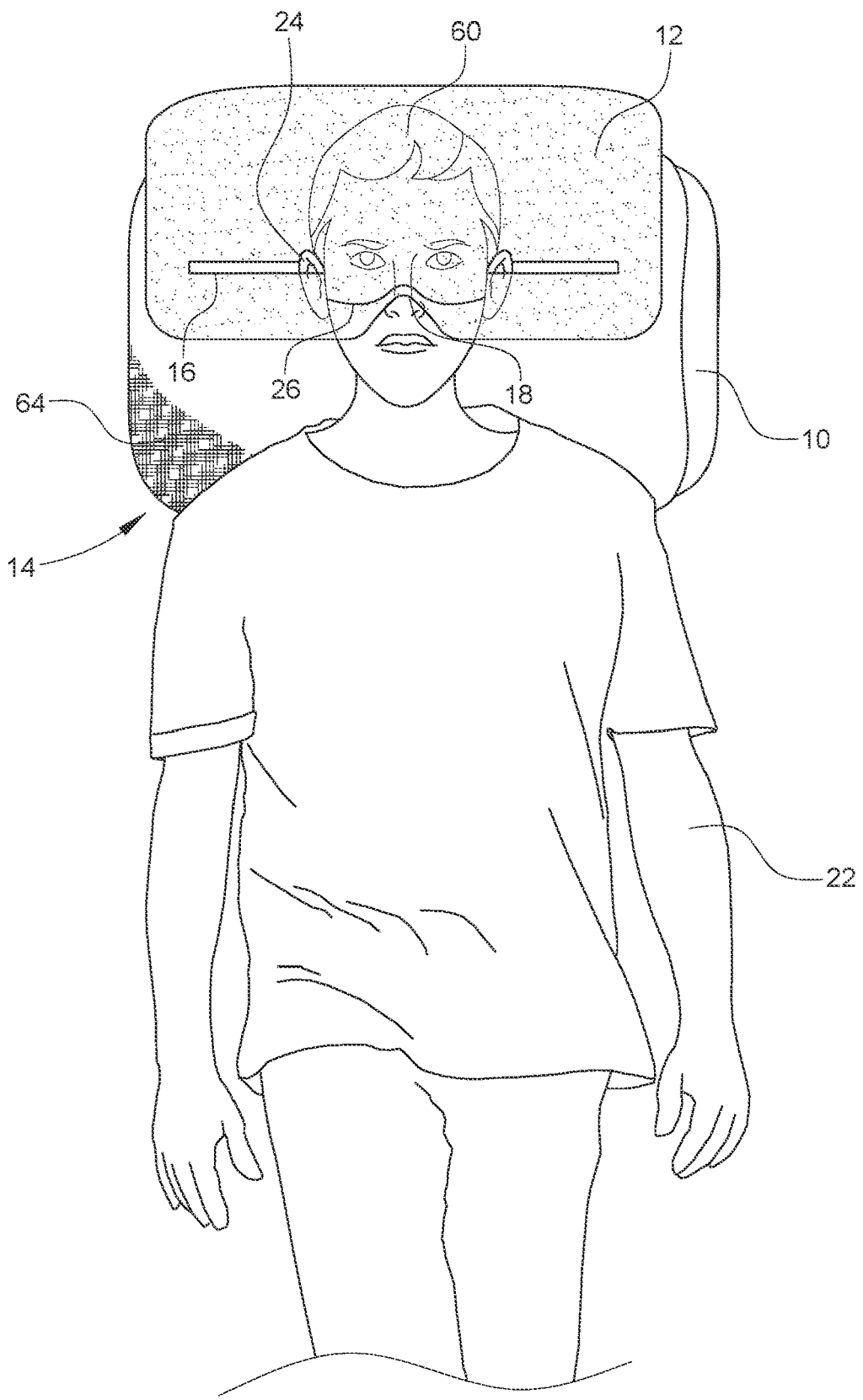
FIG. 5 illustrates another top perspective view of the preferred embodiment, depicting a person with their head resting on the pillow, covered by the blackout cover with an opening for the nose and ear slots, and the pillow itself inside the pillowcase.

FIG. 5 shows a top perspective view of a person 22 lying on a blackout pillowcase 14 with a deployed blackout cover means 12 that covers their head 60. The blackout pillowcase 14 can be made of breathable or non-breathable cotton, silk, nylon or similar materials. The blackout cover means 12, which can also be made of breathable or non-breathable materials, can be attached to or integrated into a standard pillowcase 64. The blackout cover means 12 is used to cover a person's face, including their head and eyes, to block as much as possible, light, which can disturb or hinder sleep. An opening for nose 18 is visible in this view which helps to prevent the pillowcase cover from covering the entrance to a person's nostrils. At least one optional ear slot means 16 is also shown in this view, which slips over the ear 24 as a stabilization method. The ear slot means 16 works independently or in conjunction with the opening for nose 18 to prevent the blackout pillowcase cover from slipping too far down a person's face, blocking the entrance to their nostrils. The view also shows an example of ear slot means 26 working with a nose opening to prevent the nose from being covered. A pillow 10 is visible in the image with the majority portion of said pillow slipped into a pillowcase 64. To use the blackout pillow case 14, a person only needs to pull or flip the blackout cover means 12 over their head or eyes to block out the light.

Figure 6:
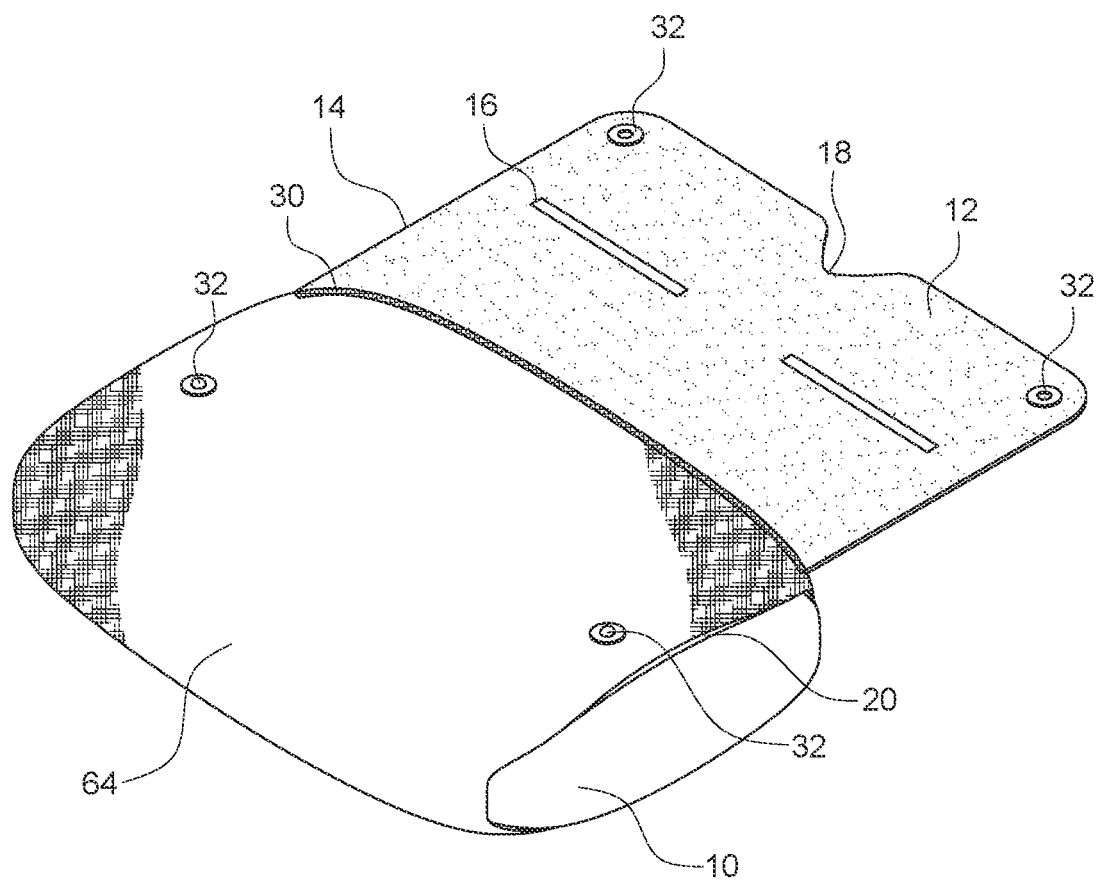
FIG. 6 illustrates a top perspective view of a version of the preferred embodiment, showing the folded open blackout cover, an opening for the nose, ear slots, the pillow, snap button attachments, an opening for the pillow, and stitches used for attachment.

Turning to FIG. 6, we see a top perspective view of the blackout pillowcase 14 with its black out cover means 12 flipped open. The blackout pillowcase is made of breathable cotton, silk, nylon, or similar materials, but can also be made of non-breathable fabrics. The blackout cover means 12 is made of breathable cotton, silk, nylon, or similar materials, but can also be made of non-breathable fabrics. It can be attached to, or integral to, a standard pillowcase 64 using a stitches means of attachment 30, which can be made of nylon, yarn, Velcro®, or any other attachment means. The blackout cover means 12 is used to cover a person's head and face, including the eyes, to block the effects of light that can disturb or hinder sleep. In this view, we also see an opening for the nose 18, which aids in stability and helps to prevent the pillowcase cover from covering the entrance to a person's nostrils. At least one optional ear slot means 16 is also present, which can slip over the ear as a stabilization method. The ear slot means works apart from, or in conjunction with, the opening for nose 18 to help prevent the pillowcase cover from slipping down a person's face to a length that blocks the entrance to a person's nostrils.

FIG. 6 also introduces a plurality of snap button means of attachments 32 that are attached to the blackout cover means 12 and also found on the actual pillowcase 64. These snap button means of attachments 32 can be used to connect the snap button means of attachment 32 found on the blackout cover means 12 to the snap button means of attachment 32 attached to the pillowcase 64. The snap button means of attachment 32 are used to help lock out the light on the edges of the pillowcase 64 when the blackout cover means 12 is deployed over a human head. Additionally, we can see the edge of a pillow 10 which slips into the pillowcase opening 20 for use.

Referring to FIG. 7, a top perspective view is shown of the right side of the side connect blackout cover means 36 which can be used as a stand-alone cover to block light or sunlight by simply placing it over the eyes, and or ears, or it can be attached to a slip on pillowcase strap overlay means 34 hook using the strap attachment means 38 made of Velcro®, cloth or similar material means. Once attached, it can be pulled or flipped over the eyes to block light or sunlight. The right side connected blackout cover means 36 is equipped with an opening for nose 18 and ear slot means 16 both of which can be used as stabilization methods for the cover. This embodiment of the present invention offers an alternate means of light blocking to a pillow or pillow case by attaching the strap attachment means to a pillowcase strap overlay means 34 hook as shown in FIG. 9.

FIG. 8 is a top perspective view of the right side of the side connect blackout cover means 36, which can be used to block light or sunlight to an optimal level by simply placing it over the eyes. The right side connected blackout cover means 36 features an opening for nose 18, ear slot means 16, and a stitches means of attachment 30 made of Velcro®, cloth or similar material means, which is used to connect the pillowcase 64 to the side connect blackout cover means 36.

Referring now to FIG. 9, it depicts an improved right side view of the side connect blackout cover means 36, which is connected to a pillowcase slip-on strap overlay means 34 hook designed for attachment purposes. The strap overlay means can be made of any suitable material, including fabric, nylon, etc. In this instance, the pillowcase strap overlay means 34 is used to link the side connect blackout cover means 36 to a strap attachment means 38. Once attached, the side connect blackout cover means 36 can be effortlessly pulled over a person's eyes, providing an effective solution for light-blocking.

FIG. 10 presents a top perspective view of the right side of the side connect blackout cover means 36. This embodiment features an opening for a nose 18, and ear slot means 16. The side connect blackout cover means 36 is attached to a pillowcase slip-on strap overlay means 34 by a strap attachment means 38. Additionally, the side connect blackout cover means 36 can also be attached to a top pillowcase slip-on strap overlay means 66 using at least one strap attachment means 38. Once attached, the side connect blackout cover means 36 can be conveniently pulled over a person's eyes to block light or sunlight.

Figure 11:
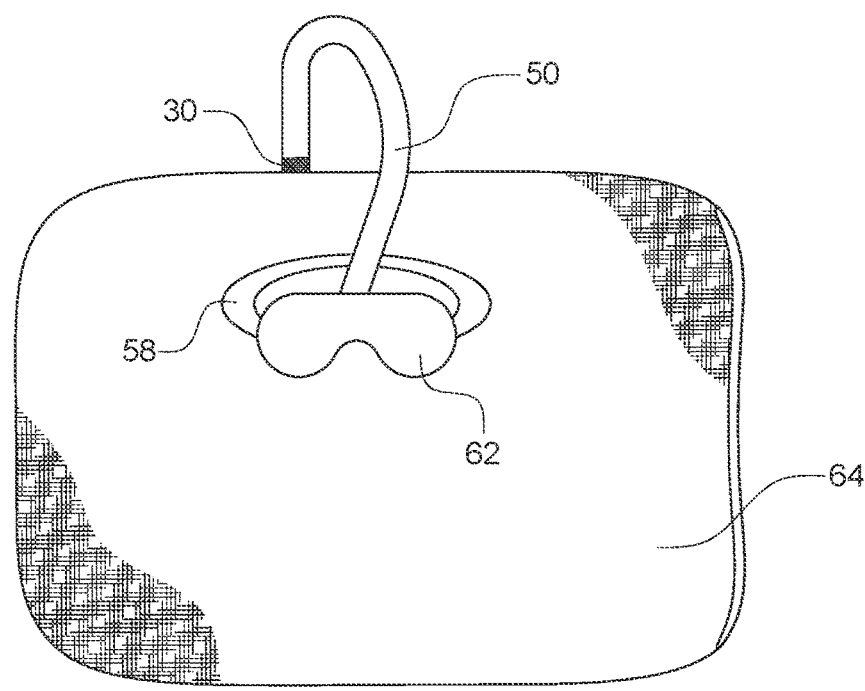
FIG. 11 illustrates a top perspective view of a pillowcase, an eye mask, a ribbon means, and an eye mask headband means in a third embodiment.

FIG. 11 depicts another embodiment of the blackout cover, which includes a pillowcase 64 connected to a ribbon means 50 made of cloth, nylon, or similar material through a stitches means of attachment 30. One end of the ribbon means 50 is also attached to an eye mask 62 via a stitches means of attachment 30. The eye mask 62 features an eye mask headband means 58 used to secure the eye mask 62 to a person's head.

Figure 12:
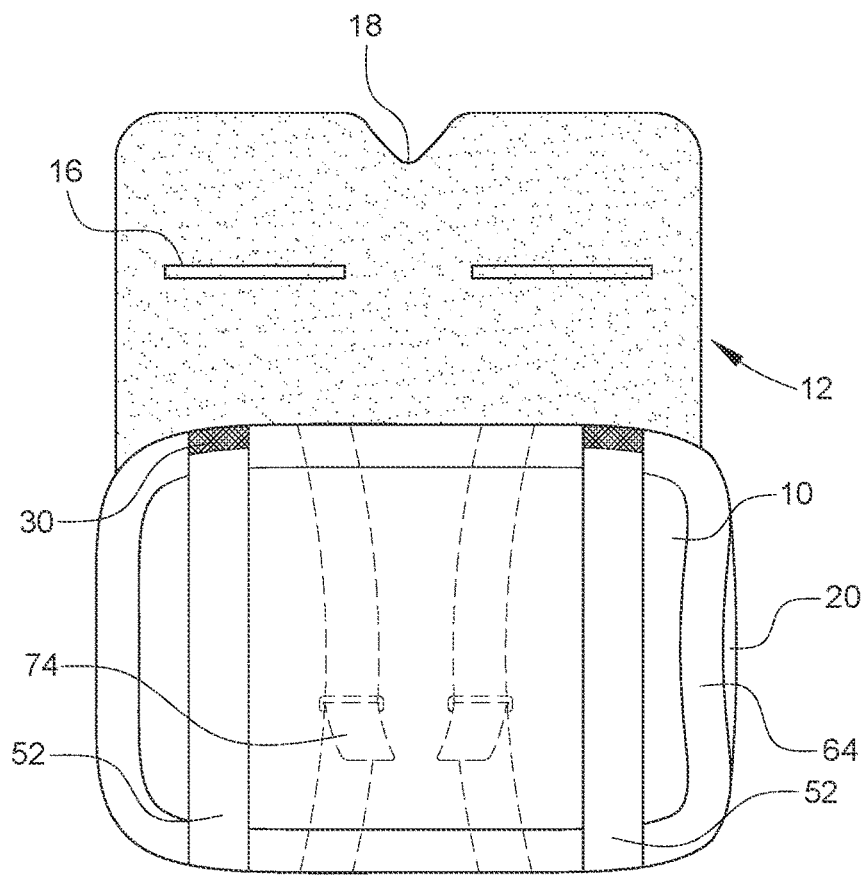
FIG. 12 illustrates a fourth embodiment of the blackout pillowcase in a top perspective view with a folded open attachable blackout cover means, a pillow, a pillowcase, a pillowcase opening, an opening for the nose, stitches means of attachment, eye slot means, and an attachable pillow loop means with an adjustable strap and slider adjustment means.

Turning to FIG. 12, we see a different embodiment of the blackout cover which features a blackout pillowcase 14 with a distinct characteristic of being able to slide onto any standard pillow or pillowcase via pillow loop means 52 made of elastic or similar material, or an adjustment slider means 74 which can be used to adjust the length of the pillow loop means 52. The blackout pillowcase 14 is made of breathable cotton, silk, nylon or similar means, but can also be made of non-breathable fabric means. The blackout cover means 12, which can also be made of breathable cotton, silk, nylon or similar means, but can also be made of non-breathable fabric means, is used to cover a person's head and face, including the eyes, to block as much light as possible, light which can disturb or hinder sleep. An opening for the nose 18 and optional ear slot means 16 are also present to help prevent the pillowcase cover from drooping down to cover the entrance to a person's nostrils, and slipping down a person's face to a length that blocks the entrance to a person's nostrils, respectively. The blackout cover means 12 is attached to a pair of pillow loop means 52 made of cloth, elastic material or nylon, which can be put around a pillow or pillowcase and attached by stitching means of attachment 30. The pillow loop means can also be attached by other suitable mechanisms such as Velcro® or snap buttons. The length of the pillow loop means 52 can be adjusted using the slider adjustment means 74. Furthermore, we can also see a pillowcase opening 20 and a pillow 10, the majority of which is slipped into a pillowcase 64.

Figure 13:
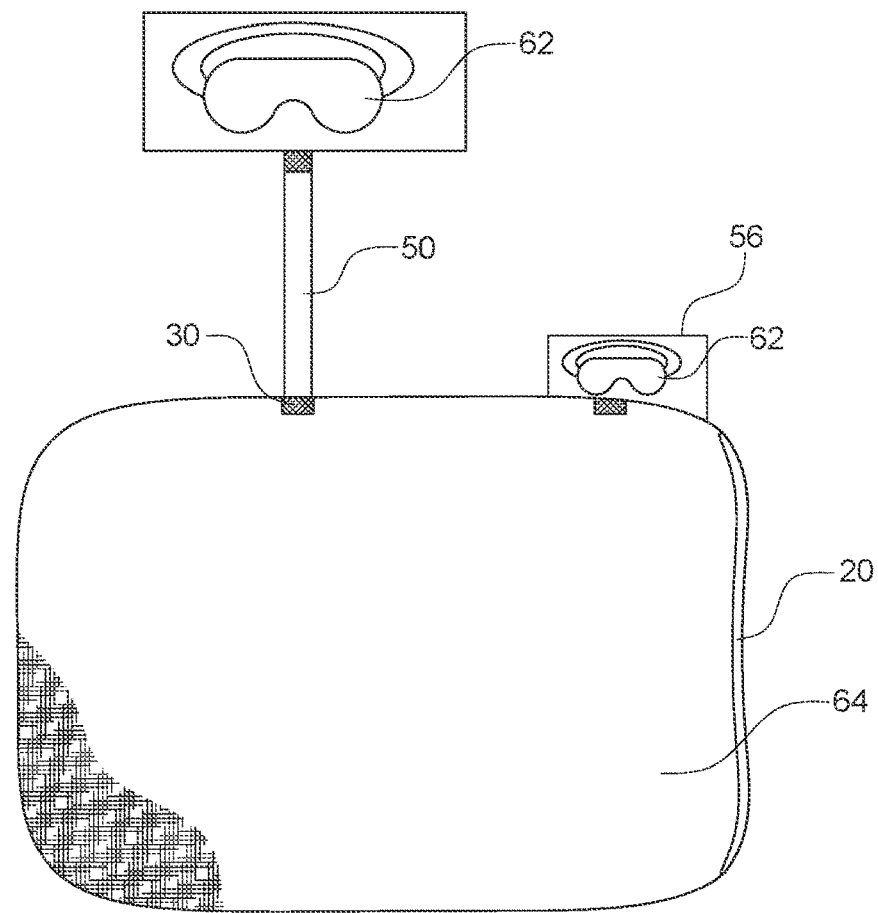
FIG. 13 illustrates a top perspective view of a pillowcase with a pillowcase opening, a ribbon means, stitches means of attachment, an eye mask case holder means, and an eye mask. This embodiment provides a convenient way to store an eye mask within the pillowcase for easy access.

FIG. 13 depicts a top perspective view of a pillowcase 64 connected to a ribbon means 50 by a ribbon means of attachment 30. At the opposite end of the ribbon means 50 and also connected by a ribbon means of attachment 30 is an eye mask case holder means 56 with an eye mask 62 appearing in it. Additionally, a pillow case opening 20 is visible in this view. To use this particular embodiment, a person simply needs to place their eye mask 62 into the eye mask case holder 56, and when needed, the user can effortlessly retrieve the eye mask 62 from the holder. The unique aspect of this embodiment is that the eye mask is readily accessible because it is attached to the pillow. Also visible in this view is an eye mask case holder means 56 that is directly attached to the pillowcase 64 by a stitches means of attachment 30, which eliminates the need for ribbon means 50. This design enables the eye mask case holder means 56 to be easily accessible, as it is attached directly to the pillowcase 64.

Figure 14:
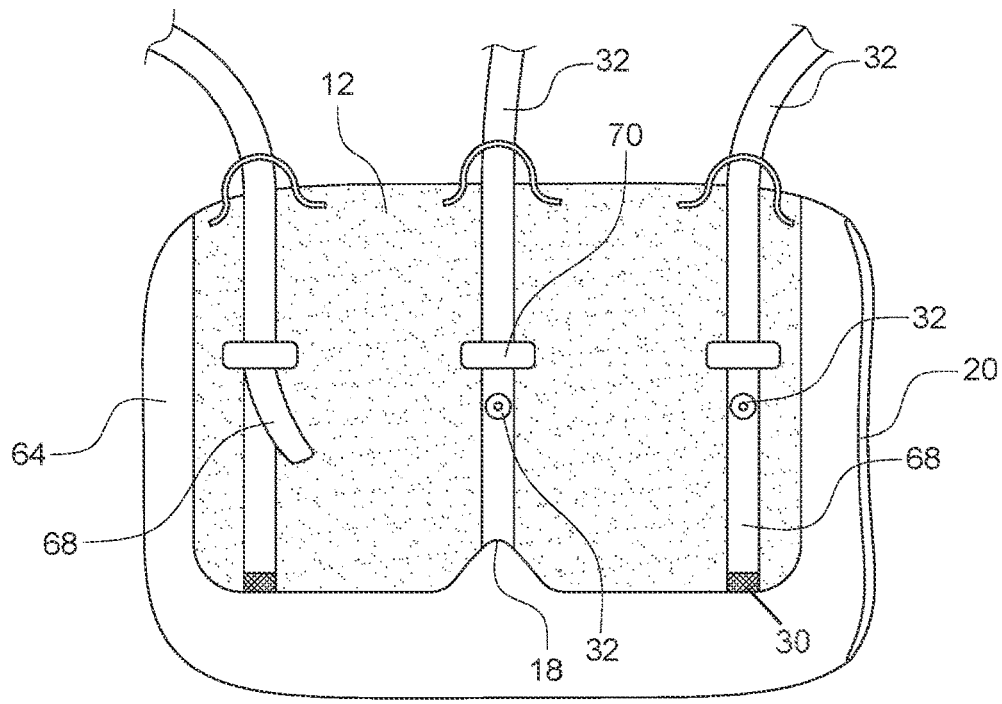
FIG. 14 illustrates a top perspective view of a customizable pillowcase with a blackout cover means that adjusts to a persons face, a pillowcase opening, adjustment straps to lengthen and shorten the cover, an opening for the nose, stitches means of attachment, strap loops, and snap button means for attachment. The adjustable strap and snap buttons provide a snug fit and ensure the blackout cover stays in place.

FIG. 14 presents a top perspective view of a pillowcase 64 with a blackout cover means 12 that is closed, revealing the exterior of the cover means. Adjacent to the cover means, adjustment straps 68 are attached to stitches means of attachment 30 on each end. These adjustment straps 68 can be threaded through strap loops 70 to allow the user to adjust the top of the blackout cover means 12 to a length suitable for their head size, ensuring that it does not obstruct their breathing. The adjustment straps 68 can also be secured in place using snap button means for attachment 32 that are present on them. The view also displays a pillowcase opening 20 and an opening for nose 18 which aids in the user's respiration while the blackout cover means is placed over their head. Ear slots 16 (seen in FIG. 12) can also still be added to this version of the blackout cover means 12.

FIG. 15 depicts a left side view of a blackout pillowcase 14 with a single layer pillowcase 64 that is connected to a multiple layer blackout cover means 12 by a stitches means of attachment 30. This view highlights an example of a blackout material means layer 72, which illustrates that the blackout pillowcase 14 and/or blackout cover means 12 can have multiple blackout layers. Additionally, a pillowcase opening is visible into which a pillow can be placed, and an optional adjustment strap 68 is shown on the blackout cover means 12 that can be utilized in conjunction with the strap loops 70 to modify the length of the blackout cover means 12. The adjustment straps 68 can also be secured in place by means of snap button attachment means 32 found on the adjustment straps 68.

Figure 16:
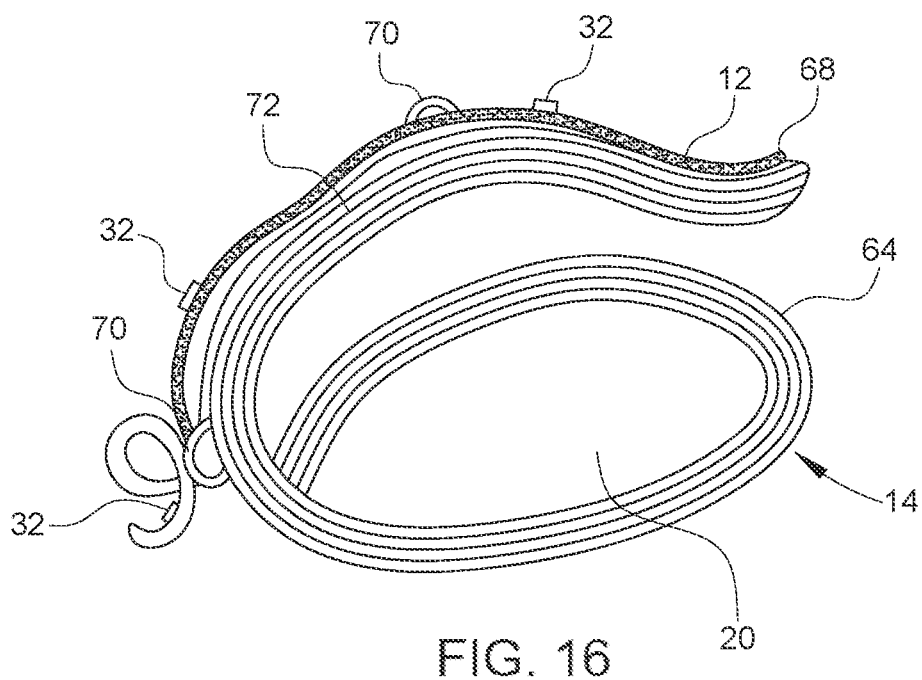
FIG. 16 illustrates a left side view of an embodiment featuring a multiple layer blackout pillowcase and a multiple layer pillowcase. The pillowcase has a pillowcase opening, and both the pillowcase and blackout cover have multiple layers of blackout material means for maximum light blocking. The embodiment also includes a nose opening and optional adjustment strap, strap loops, and snap button means for secure attachment. This embodiment provides a solution for those who want to sleep in significant darkness by blocking out maximum light with multiple layers of blackout material. This embodiment demonstrates that the blackout pillowcase and cover can be made of one flowing material.

FIG. 16 depicts a left side view of a blackout pillowcase 14 with an integrated multiple layer blackout out cover means 12 that is also a multiple layer pillowcase 64. This view includes a demonstration of a blackout out material means layer example 72, highlighting the potential for multiple blackout layers in the blackout pillowcase 14 and/or blackout cover means 12. In addition, a pillowcase opening 20 is visible for the placement of a pillow. An optional adjustment strap 68 is present on the blackout cover means 12, which can be utilized in combination with the strap loops 70 to adjust the length of the blackout cover means 12. Furthermore, the adjustment straps 68 can be secured in place by snap button means for attachment 32 located on the adjustment straps 68.

Unless otherwise defined, all terms (including technical terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

The disclosed embodiments are illustrative, not restrictive. While specific configurations of the blackout cover apparatus have been described in a specific manner referring to the illustrated embodiments, it is understood that the present invention can be applied to a wide variety of solutions which fit within the scope and spirit of the claims. There are many alternative ways of implementing the invention.

It is to be understood that the embodiments of the invention herein described are merely illustrative of the application of the principles of the invention. Reference herein to details of the illustrated embodiments is not intended to limit the scope of the claims, which themselves recite those features regarded as essential to the invention.

LIST OF REFERENCE NUMERALS

- 10 pillow
- 12 blackout cover means
- 14 blackout pillowcase
- 16 ear slot means
- 18 opening for nose
- 20 pillowcase opening
- 22 person
- 24 ear
- 26 ear slot means working with nose opening
- 30 stitches means of attachment
- 32 snap button means of attachment
- 34 pillowcase strap overlay means
- 36 side connect blackout cover means
- 38 strap attachment means
- 42 elastic edge means
- 50 ribbon means
- 52 pillow loop means
- 56 eye mask case holder means
- 58 eye mask headband means
- 60 head
- 62 eye mask
- 64 pillowcase
- 66 top pillowcase strap overlay means
- 68 adjustment strap
- 70 strap loops
- 72 blackout material means layer example
- 74 slider adjustment means

What is claimed is:

1. A blackout cover apparatus for a pillowcase, the apparatus comprising:
   a detachable blackout cover means;
   an attachment mechanism specifically configured for coupling the blackout cover means to a surface of the pillowcase, the attachment mechanism comprising one or more loops encircling the pillowcase;
   wherein the one or more loops are elastic and adjustable in length; and
   wherein the one or more loops are adjusted by a slider adjustment means, the one or more loops and the slider adjustment means are configured to adjust the length of the blackout cover means thereby increasing or decreasing an area of the pillowcase that is covered by the blackout cover means.

2. A blackout cover apparatus according to claim 1, wherein the blackout cover means comprises a fabric cover.

3. A blackout cover apparatus according to claim 2, wherein the fabric cover comprises one or more openings for the ears, mouth, or nose.

4. A blackout cover apparatus according to claim 2, wherein the fabric cover is formed of a breathable material.

5. A blackout cover apparatus according to claim 2, wherein the perimeter of the fabric cover is elastic.

6. A blackout cover apparatus according to claim 1, further comprising one or more snap button fittings for securing portions of the blackout cover means to the pillowcase.

7. A blackout cover apparatus according to claim 1, wherein the blackout cover means is a material selected from the group consisting of: silk, cotton, and nylon.

* * * * *